United States Patent
Le Blanc

(10) Patent No.: US 12,268,396 B2
(45) Date of Patent: Apr. 8, 2025

(54) WEARABLE SAFETY TOURNIQUET ASSEMBLY FOR CHAINSAW CHAPS

(71) Applicant: Eric Le Blanc, Murrieta, CA (US)

(72) Inventor: Eric Le Blanc, Murrieta, CA (US)

(*) Notice: Subject to any disclaimer, the term of this patent is extended or adjusted under 35 U.S.C. 154(b) by 791 days.

(21) Appl. No.: 17/395,165

(22) Filed: Aug. 5, 2021

(65) Prior Publication Data
US 2023/0038923 A1     Feb. 9, 2023

(51) Int. Cl.
| | |
|---|---|
| *A61B 17/132* | (2006.01) |
| *A41D 13/05* | (2006.01) |
| *A41D 17/00* | (2006.01) |
| *A61B 17/00* | (2006.01) |

(52) U.S. Cl.
CPC ....... *A61B 17/1327* (2013.01); *A41D 13/0543* (2013.01); *A41D 13/0568* (2013.01); *A41D 17/00* (2013.01); *A41D 2300/20* (2013.01); *A41D 2600/20* (2013.01); *A61B 2017/00858* (2013.01)

(58) Field of Classification Search
CPC ........ A61B 17/132; A61B 2017/00858; A61B 17/1327; A61B 2017/00119; A61B 90/98; A61B 17/1322; A61B 17/1325; A41D 13/0543; A41D 13/0568; A41D 2600/20; A61D 17/00; A61D 2300/20
See application file for complete search history.

(56) References Cited

U.S. PATENT DOCUMENTS

| | | | |
|---|---|---|---|
| 2014/0230116 A1* | 8/2014 | Weber | A41D 13/0543 2/22 |
| 2021/0100298 A1* | 4/2021 | Levesque | A41D 31/245 |

OTHER PUBLICATIONS

Messenger et al., USDA Tech Tips 5100/6700 0451-2324P-MTDC Jun. 2004 ((www.fs.usda.gov/sites/default/files/2019-12/tech-tip-chaps.pdf), Last Accessed Apr. 23, 2024) (Year: 2004).*
ASTM F1897-2020 Standard Specifications for Leg Protection for Chainsaw Users (www.astm.org/f1987-20.html (Jan. 1, 2020), Last Accessed Apr. 22, 2024). (Year: 2020).*
Husqvarna Technical Apron Wrap Chainsaw Chaps (www.Husqvarna.com/us/work-wear/technical-apron-wrap-chainsaw-chaps. Jun. 21, 2016 (for sale on Amazon.com). Last Accessed Apr. 22, 2024) (Year: 2016).*
Sawyer Bleeding Control Kit: Rescue Essentials (www.rescue-essentials.com/sawyer-bleeding-control-kit). Mar. 23, 2018 (Google Search Results). Last Accessed Apr. 22, 2024 (Year: 2018).*

* cited by examiner

*Primary Examiner* — Tan-Uyen T Ho
*Assistant Examiner* — Cherie M Poland

(57) ABSTRACT

Embodiments of the present disclosure relate to a wearable safety tourniquet assembly. The assembly provides a safety tourniquet that circumferentially integrates into a pair of chainsaw chaps for applying pressure to an injured limb. The safety tourniquet has a resilient strap that circumferentially integrates into the limb sections of the chaps. The strap is configured to wrap around the limb of the wearer directly, and without separation from the chaps. The safety tourniquet also has one or more tensioning mechanisms that are operatively attached to the strap.

18 Claims, 14 Drawing Sheets

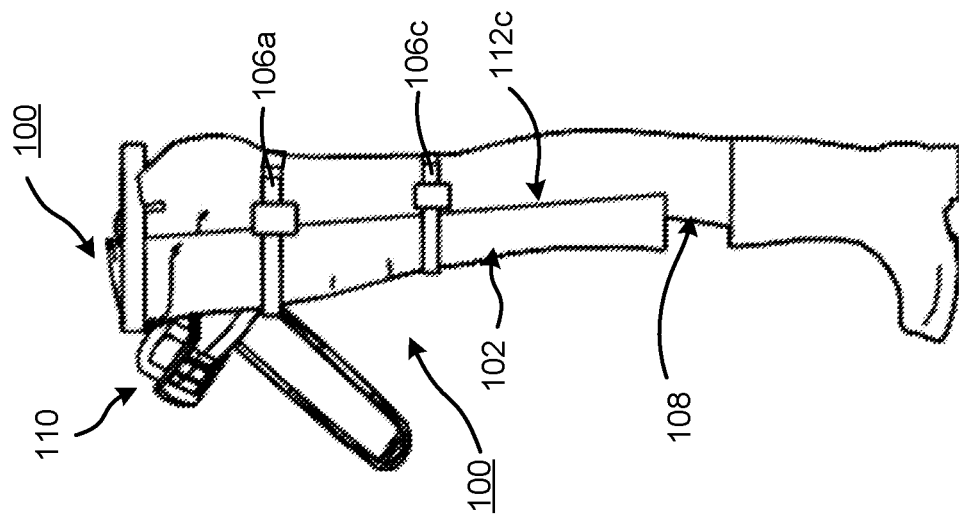
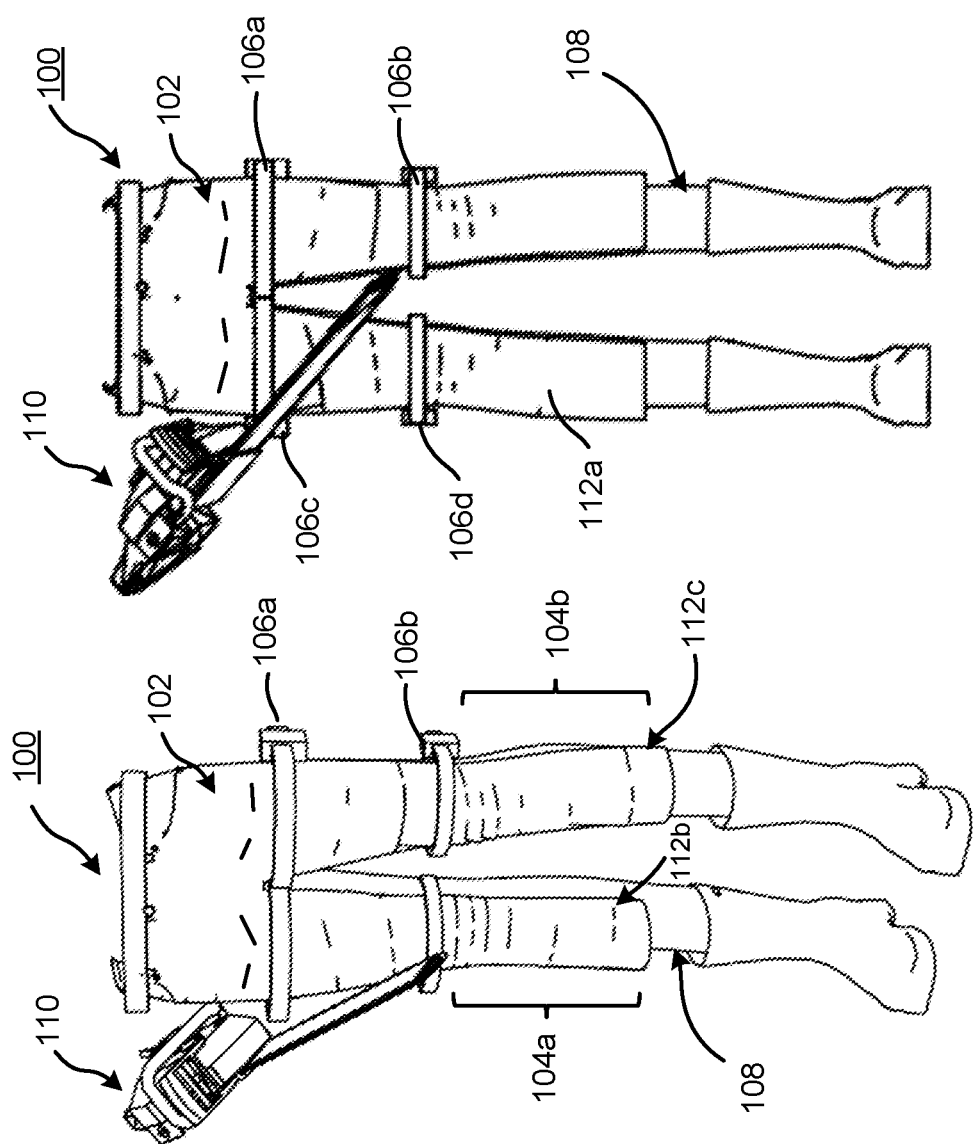
FIG. 1C
FIG. 1B
FIG. 1A

WEARABLE SAFETY TOURNIQUET ASSEMBLY FOR CHAINSAW CHAPS

FIELD OF THE INVENTION

The present disclosure relates to a wearable safety tourniquet assembly for chainsaw chaps. More so a tourniquet assembly includes a safety tourniquet, having a strap and one or more tensioning mechanisms, for applying pressure to an injured limb; whereby the safety tourniquet circumferentially integrates into the limb sections of the chainsaw chaps.

BACKGROUND

The following background information may present examples of specific aspects of the prior art (e.g., without limitation, approaches, facts, or common wisdom) that, while expected to be helpful to further educate the reader as to additional aspects of the prior art, is not to be construed as limiting the present disclosure, or any embodiments thereof, to anything stated or implied therein or inferred thereupon.

Typically, the loss of blood is a major cause of death in emergency situations in which the injured person is alone or medical assistance is not immediately available. The use of a tourniquet to stop blood loss from an injured arm or leg is a well-known technique for preventing death in these situations. In general, for emergency use where the victim is alone, the victim must be able to apply the tourniquet to his or her own arm or leg and occlude blood flow using only one hand.

In many instances, tourniquets generate inward compression on the limb by being put into high levels of circumferential tension when wrapped around the limb.

By applying a tourniquet, blood flow is restricted to the injured limb to prevent life-threatening blood loss. While constricting the limb to cut off its blood supply is a temporary measure, when done correctly it will slow or stop the bleeding enough to allow emergency responders time to arrive at the scene.

It is known that tourniquets can be made out of any available material. For example, a bandage, strip of cloth, or even a t-shirt. Tourniquets often use a windlass device that attaches to the free ends of the tourniquets and is twistable, so as to increase tightening. The tourniquet is often placed between the injured vessel and the heart.

Accordingly, there is a need for an emergency, lightweight tourniquet that provides improved pressure to the wounded limb, thereby restricting blood flow to the limb. Furthermore, there is a need for such a tourniquet that can be applied by the victim using one hand.

SUMMARY

A wearable safety tourniquet assembly provides a strap that circumferentially integrates into a pair of chaps for applying pressure to an injured limb; and thereby occluding blood flow through the limb. The chaps have a front face, an inner face, and an outer face. In some embodiments, the strap circumferentially, and fixedly, integrates into the limb sections of the chaps. Once integrated in this manner, the strap can wrap around the limb of the wearer directly, and without separation from the chaps.

The safety tourniquet also has one or more tensioning mechanisms configured to tighten and loosen the strap around the limb. The tensioning mechanisms are operatively attached to the free ends of the strap. The tensioning mechanisms are oriented to protrude from the outer face of the limb sections of the chaps. This fixed, outer-facing disposition of the tensioning mechanism in relation to the chaps serves to facilitate access to the tensioning mechanism, and minimize the risk of the tensioning mechanism being damaged by the blades of the chainsaw.

In one aspect, the wearable safety tourniquet assembly may include a protective garment having multiple elongated limb sections configured to encircle and protect limbs of a wearer, the limb sections having a front face, an inner face, and an outer face, and multiple safety tourniquets, each safety tourniquet having a resilient strap being circumferentially and fixedly integrated into the limb sections of the protective garment, the strap operable to wrap around a portion of each limb of the wearer; and a tensioning mechanism being operatively connected to the strap, the tensioning mechanism being oriented towards the outer face of the limb sections. In addition, the tensioning mechanisms may be configured to tighten the strap around each limb to stem the flow of blood.

In another aspect, the wearable safety tourniquet assembly, may have a pair of chaps including multiple elongated leg sections configured to encircle and protect legs of a wearer, the leg sections having a front face, an inner face, and an outer face, and multiple safety tourniquets, each safety tourniquet having a resilient strap being circumferentially and fixedly integrated into the leg sections of the chaps, the strap operable to wrap around a portion of each leg of the wearer; and a tensioning mechanism being operatively connected to the strap, the tensioning mechanism being oriented towards the outer face of the leg sections. Also, the tensioning mechanisms may be configured to incrementally tighten the strap around each leg to stem the flow of blood.

In other embodiments, the tensioning mechanism can be interchanged to accommodate different pressure requirements, spacing around the chaps, and material and budgetary parameters.

In alternative embodiments, a medical kit and/or a sanitization pouch, detachably joins the chaps. The medical kit and sanitization pouch can be attached to an exterior surface of the chaps, or fitted into a pocket on the chaps, for easy retrieval thereof.

In operation, the wearer dons the pair of chaps, including the integrated strap and tensioning mechanism. Upon accidental engagement with the blade of a chainsaw, the user can identify the location of the injured limb, adjust the strap between the injury and the heart, and then twist the tensioning mechanism to tighten the strap around the limb. This tightening helps to occlude blood flow towards the heart. Uniquely, the safety tourniquet is self-operable by the wearer of the chaps, which enables immediate restriction of blood flow if an accident occurs while wearing the chaps.

One objective of this disclosure is to provide a tourniquet assembly for chainsaw chaps.

Another objective is to enable operation of the safety tourniquet while donning the chaps.

Yet another objective is to enable access to the tensioning mechanisms from the outer face of the chaps, or outer region of the limbs, so as to facilitate access, and minimize risk of damage to the tensioning mechanism from the blades of the chainsaw.

Yet another objective is to make chainsaw operations safer.

Yet another objective is to enable one-handed operation of the tensioning mechanism.

Yet another objective is to enable interchangeability of the tensioning mechanism.

Yet another objective is to provide a medical kit that works in conjunction with the safety tourniquet.

Yet another objective is to provide an inexpensive to manufacture wearable safety tourniquet assembly.

These and other objects, features and advantages of the present disclosure will become more apparent in light of the following detailed description of preferred embodiments thereof, as illustrated in the accompanying drawings.

BRIEF DESCRIPTION OF THE DRAWINGS

Although the characteristic features of the present disclosure will be particularly pointed out in the claims, the disclosure itself and manner in which it may be made and used may be better understood after a review of the following description, taken in connection with the accompanying drawings wherein like numeral annotations are provided throughout.

FIGS. 1A-1C illustrates an exemplary wearable safety tourniquet assembly integrated into a pair of chainsaw chaps, where FIG. 1A shows a frontal perspective view, FIG. 1B shows a front view, and FIG. 1C shows an elevated right-side view, in accordance with an embodiment of the present disclosure;

FIG. 4A shows the free end of the strap detached from the tensioning mechanism, and FIG. 4B shows the free ends of the strap coupled to the tensioning mechanism for operation, in accordance with an embodiment of the present disclosure;

DETAILED DESCRIPTION

Figure 2:
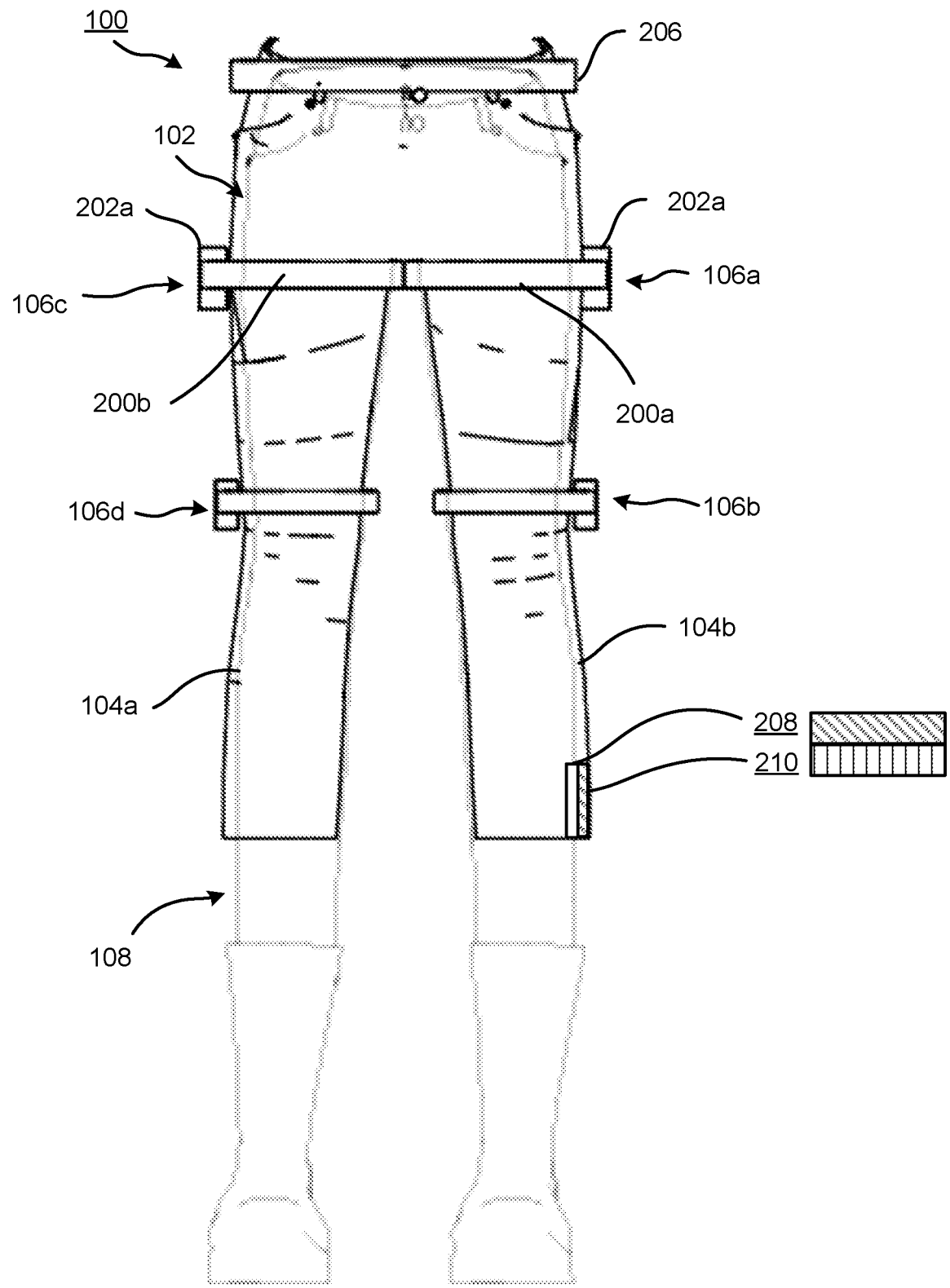
FIG. 2 illustrates a perspective view of another wearable safety tourniquet assembly, showing a close up of a tensioning mechanism and strap, and a cloth layer and impact resistant layer that make up the protective garment, in accordance with an embodiment of the present disclosure.

The present disclosure provides a wearable safety tourniquet assembly for chainsaw chaps.

FIG. 1A illustrates a wearable safety tourniquet assembly 100 for chainsaw chaps. The wearable safety tourniquet assembly 100, hereafter "assembly 100" uniquely integrates a safety tourniquet 106a-d into the leg sections of a pair of chainsaw chaps, and provides multiple types of tensioning mechanisms 202a-b that can tighten or loosen a strap 200a-b around the limb of the wearer 108. As illustrated, a wearer 108 operates a chainsaw 110 while donning the assembly 100, such that if the limb is cut by the blade of the chainsaw 110, the safety tourniquet 106a-d is easily accessed by the wearer 108 from the outer region of the limb, so as to stem the flow of blood through the cut limb.

As referenced in FIG. 1B, the assembly 100 includes a protective garment 102 that is wearable, often, while performing dangerous activities. In one non-limiting embodiment, the protective garment 102 is a pair of chainsaw chaps, often worn while operating a chainsaw 110. However, in alternative embodiments, the protective garment 102 can be an apron, a vest guard, or a full body suit. Any type of protective and wearable garment that protects against physical impact, heat, extreme cold, and radiation may be used for the present disclosure.

Those skilled in the art will recognize that operating a chainsaw 110 may result in kickback, which abruptly drives the blades of the chainsaw 110 towards the lower limbs of the user. Thus, protection is important for the lower limbs, such as the legs and lower torso.

In one non-limiting embodiment, the protective garment 102 includes multiple elongated limb sections 104a-b that are configured to at least partially encircle multiple limbs, when donned by the wearer 108. The limb sections 104a-b can include a left limb section 104b for protecting the left leg, and a right limb section 104a for protecting the right leg. The limb sections 104a-b are configured to at least partially wrap around the limbs from the front, inner, and outer regions of the limbs. The limb sections 104a-b, when donned by the wearer 108, have a front face 112a, an inner face 112b, and an outer face 112c. In one possible embodiment, the front face 112a orients and covers the front thigh, or quad of a leg. The inner face 112b orients towards the inner thigh. And the outer face 112c which is significant for the present disclosure, orients towards the outer region 114 of the leg or thigh.

For example, when covering the legs, the limb sections 104a-b at least partially encircle the legs of the wearer 108, from the waist to the ankle region of the wearer. Specifically, the limb sections 104a-b can be designed to at least partially encircle the legs from the top of the foot to the crotch and extending along a longitudinal line from the crotch to the sides of a wearer 108 at the waist.

It is significant to note that the faces 112a-c of the limb sections 104a-b can also orient to similar anatomical regions of the arms, torso, neck, and other body parts. For example, in alternative embodiments, a protective garment is configured to cover a portion of the upper body, including the arms, torso, and neck. Thus, it is possible that the limb sections 104a-b at least partially encircle the arms, the torso and the neck.

Additionally, the protective garment 102, when arranged as a pair of chaps, can include a front torso section that covers the front of the body above the thighs, and a waist section 206 that encircles the waste of the wearer 108 (See FIG. 1B). It is known in the art that chaps generally do not have a rear seat. However, in alternative embodiments, the protective garment 102 does include a rear seat to cover the buttocks area of the wearer.

As discussed above, the protective garment 102 is effective for protecting against physical impact, such as kickback from a chainsaw 110 that can cut through the legs of the chainsaw operator. Thus, as illustrated in FIG. 2, the limb sections 104a-b of the protective garment 102 may comprise at least one cloth layer 210, and at least one impact resistant layer 208. The impact resistant layer 208 serves as the primary protection against the blades of the chainsaw 110. The cloth layer 210 overlays the impact resistant layer 208.

In one possible embodiment, the impact resistant layer 208 comprises a fibrous material that is resistant to the blades of a chainsaw, and further, adapted to jam the mechanism of a chainsaw blade cutting through the cloth layer 210. As discussed below, multiple safety tourniquets 106a-d integrate into the limb sections 104a-b, between the different layers 208, 210 of the protective garment 102. The safety tourniquets 106a-d are fixedly integrated into the protective garment, and oriented to enable easy access and protection from damage by the chainsaw blades, as discussed below.

As illustrated in FIG. 2, the assembly 100 provides multiple safety tourniquets 106a-d that integrates into the limb sections 104a-b of the protective garment 102. In one possible embodiment, two safety tourniquets 106a, 106b are arranged in a spaced-apart relationship along the longitudinal of the left limb section 104b; and two safety tourniquets 106c, 106d are arranged in a spaced-apart relationship along the longitudinal of the right limb section 104a.

The spaced apart relationship of safety tourniquets 106a-d is advantageous for restricting the flow of blood, generally between an upper and lower region of the legs. However, in alternative embodiments, additional safety tourniquets may be used along different sections of the legs, arms, or other parts of the body. In any case, the safety tourniquets are fixedly integrated into the limb sections of the protective garment.

In some embodiments, the safety tourniquet 106a-d comprises a resilient strap 200a-b that is circumferentially integrated into the limb sections 104a-b of the protective garment 102. In other embodiments, multiple safety tourniquets 106a, 106b, 106c, 106d can be used simultaneously across the limb sections 104a-b of the protective garment. This multi-tourniquet configuration is described below.

In one non-limiting embodiment, the strap 200a-b integrates between the cloth layer 210 and the impact resistant layer 208 of the protective garment 102. In some embodiments, the position of the strap 200a-b in the protective garment 102 enables facilitated wrapping of the strap 200a-b around the limbs. Thus, the strap 200a-b traverses at least one cross-section across the length of the limbs section. In another embodiment, a portion of the resilient strap 200a-b may be woven inside the protective garment 102, disposed underneath or in between the cloth layer 210 and the impact resistant layer 208. In yet another embodiment, a portion of the resilient strap 200a-b may be wrapped or enclosed inside a cut resistant protective sleeve or jacket, protecting the strap 200a-b from being damaged or sliced through by the chainsaw. In another embodiment, multiple impact resistant layers 208 may be applied to any portion of the chaps for additional protection to the wearer of the chaps.

As FIG. 1C shows, multiple straps can be arranged to traverse the cross-section of the limb sections 104a, 104b. For example, a first strap could wrap around the ankle, while a second strap can wrap around the upper thigh. The second strap 200a-b would be longer, and possibly denser to accommodate the larger muscle of the thigh. Or, as illustrated, two straps could be arranged in a spaced-apart parallel relationship.

In alternative embodiments of the assembly, the strap 200a-b is actually part of the garment. In this configuration, fibers in the strap 200a-b are part of the fibers in the protective garment 102. However, the fibers in the strap 200a-b are denser, which creates a strap-like characteristic across that cross-section. Furthermore, in this integrated strap 200a-b configuration, free ends that connect to the integrated strap 200a-b pass through openings in the protective garment 102 for attachment to the tensioning mechanisms 202a-b, described below.

In exemplary use, the strap 200a-b is located along the limbs section in a more proximal location to the heart, than the joints of the limb. Thus, the strap 200a-b serves as a barrier of sorts to the heart. This is because the objective of a tourniquet is to prevent surges of blood flow from reaching the heart.

In one possible embodiment, the strap 200a-b is fabricated from a stretchable, rubber material that stretches to accommodate variously sized limbs i.e., legs and thighs. The strap 200a-b can also be fabricated from a nonwoven fabric, a polymer, or a natural fiber. The length of the strap 200a-b is sufficient to enable wrapping around a human limb, and also have sufficient extra length to enable twisting to create torque, and thereby creating pressure on the limb.

Figure 3:
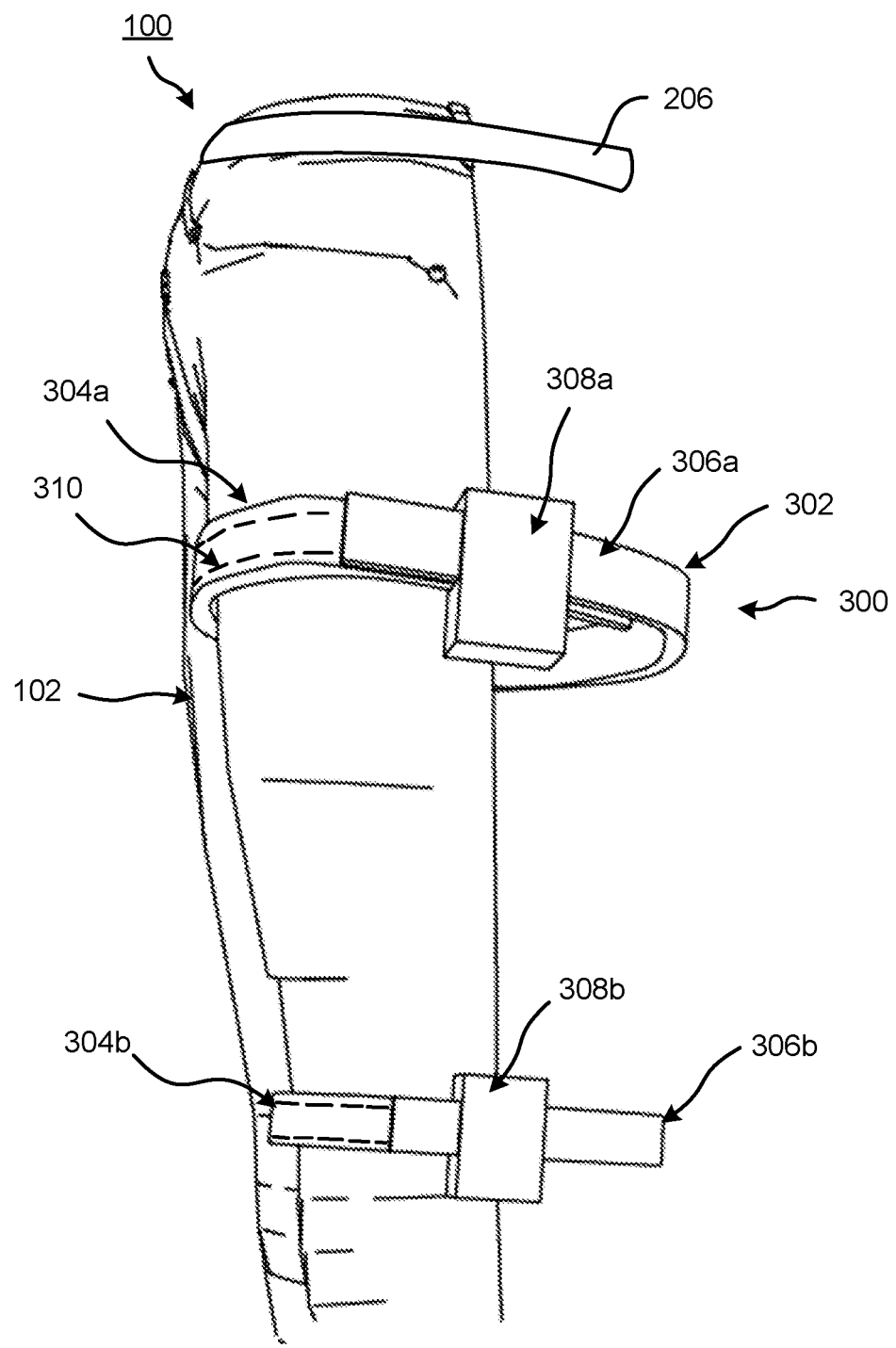
FIG. 3 illustrates a right-side perspective view of an exemplary safety tourniquet showing a strap having a back side fixedly sewn into the protective garment, and a front side coupled to the tensioning mechanism, in accordance with an embodiment of the present disclosure.

One possible embodiment of a safety tourniquet 300 utilizes a strap 302 that is segregated between a front side 304a, 304b and an opposing back side 306a, 306b. The front side 304a-b orients towards the front face 112a of the limb sections 104a-b, as described above. FIG. 3 illustrates such a safety tourniquet showing a strap 302 having a back side 306a-b fixedly sewn into the protective garment, and a front side 304a-b coupled to the tensioning mechanism 308a.

In some embodiments, the front side 304a-b of strap 302 is sewn into the fabric of the protective garment 310. As illustrated, the dashed lines indicate sewing 310, or welding, along the longitudinal of the strap 302. This fixed configuration restricts the strap 302 from moving circumferentially or longitudinally, relative to the limb sections 312a, 312b.

Furthermore, such a fixed relationship ensures that the safety tourniquet 300 remains at the optimal pressure points for restricting the flow of blood. The back side 306a-b of the strap 302 that is configured to couple to a tensioning mechanism 308a, 308b, described below. In some embodiments, the back side 306a-b has a pair of free ends that couple, or otherwise insert, into the tensioning mechanism 308a-b, depending on the type of tensioning mechanism used. Thus, the strap 302 fixedly joins the protective garment from the front side 304a-b of strap 302, and couples to the tensioning mechanism 308a-b from the back side 306a-b of strap 302.

Figure 5:
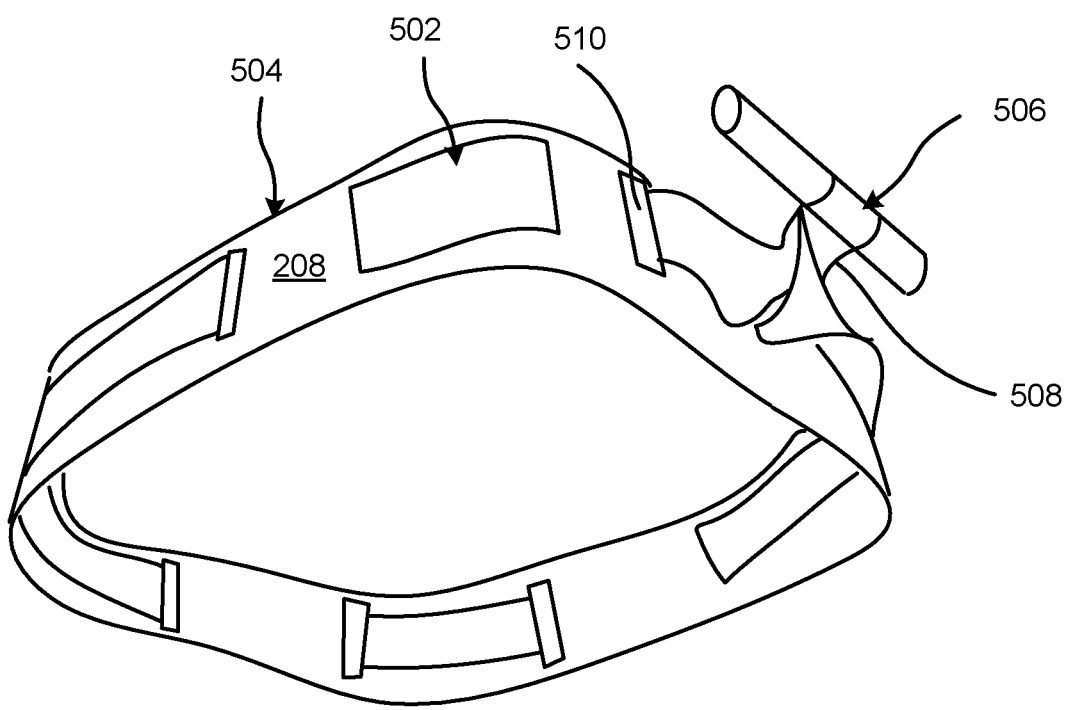
FIG. 5 illustrates a perspective view of an exemplary safety tourniquet consisting of a simple lever and cloth strap, in accordance with an embodiment of the present disclosure.

In alternative embodiments, shown in FIG. 5, a safety tourniquet 500 utilizes a strap 502 that weaves through an elongated sleeve 504 of the impact resistant layer material 208. The sleeve 504 serves to protect the strap 502 from being cut by the chainsaw blade, or other impactful force. Nonetheless, whether the strap 502 is protected, or unprotected, the free ends 510 of the strap are configured to couple 508 to a tensioning mechanism 506, which serves to tighten and loosen the strap 502 around the limb.

In another alternative embodiment, the strap is characterized with a bladder configuration, operatively attaching to an air pump. The air pump is configured to inflate the strap to a desired pressure, i.e, psi. Inflating the strap in such a manner creates greater pressure on the limb. In this manner, both the tensioning mechanism and the air pump can tighten and loosen the strap around the limb more precisely.

Figure 4A:
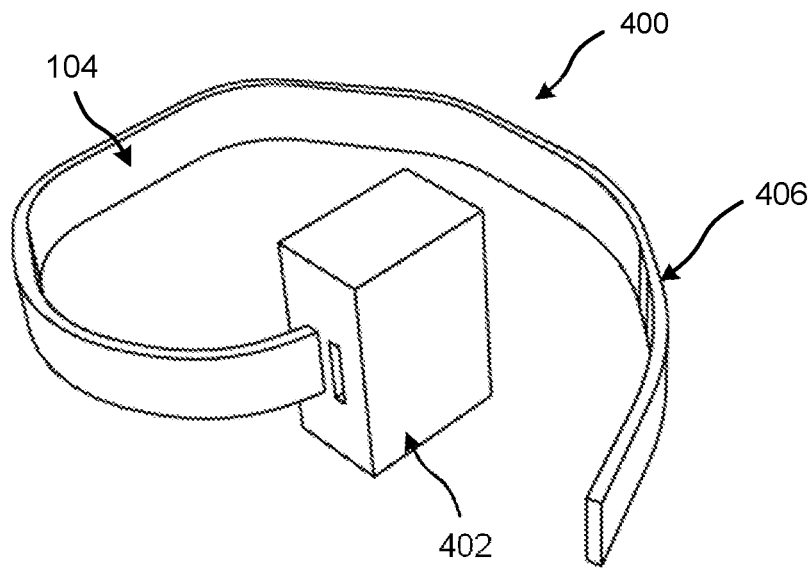
FIGS. 4A-4B illustrate an exemplary strap and tensioning mechanism, where
Figure 4B:
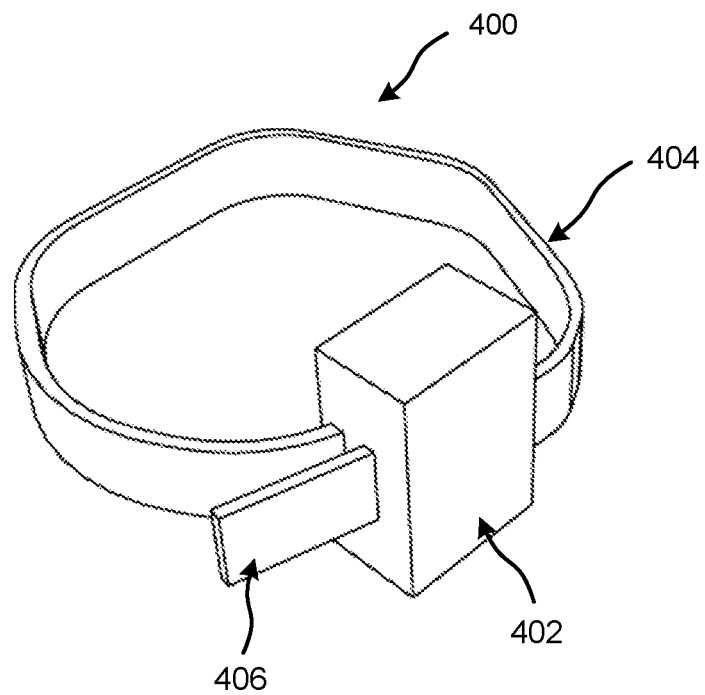

Looking now at FIGS. 4A-4B, a safety tourniquet 400 comprises has a tensioning mechanism 402 that is operable with a strap 404 to tighten and loosen the strap 404 around the limb. In one embodiment, the tensioning mechanism 402 is operatively attached to the free ends of the strap 404, so as to lengthen and shorten the length of the strap through various means. For example, FIG. 4A shows one free end 406 of the strap 404 disengaged from the tensioning mechanism 402. And FIG. 4B shows the free end 406 of the strap 404 coupled to the tensioning mechanism 402, creating a loop that allows the tensioning mechanism 402 is operable to tighten and loosen the strap 404 around the limbs.

Looking again at FIG. 2, the tensioning mechanism 202a-b is oriented to protrude from the outer face 112c on the limb sections of the protective garment 102 (See FIGS. 1A-1C). This fixed, outer-facing disposition of the tensioning mechanism 202a-b in relation to the protective garment 102 serves to facilitate access to the tensioning mechanism 202a-b, as the wearer 108 can simply reach down to the natural position for gripping and manipulating the tensioning mechanism 202a-b.

Furthermore, the outer-facing disposition of the tensioning mechanism minimizes the risk of damage by the blades of the chainsaw. It is known in the art that when a chainsaw 110 kicks back, the blades will strike the front face 112a or inner face 112b of the limb sections. Thus, the outer-facing disposition helps protect the tensioning mechanism 202a-b from damage.

In some embodiments, the tensioning mechanisms 202a-b are used to or tighten and loosen the strap around the limb, while the strap 200a-b itself is integrated into the limb section of the protective garment 102. For example, the strap 200a-b can have two free ends that path out of the protective garment 102 through at least one opening. The free ends of the strap are operatively connected to the tensioning mechanism 202a-b, such that manipulation of the tensioning mechanism—often through rotation—serves to tighten or loosen the strap 200a-b around the limb.

In one possible embodiment, the tensioning mechanism 202a-b can be manually manipulated to tighten and loosen the strap that is integrated into a chainsaw 110, and wrapped around the leg. For example, if the free ends of the strap 200a-b are twisted, this creates a shorter length along the strap 200a-b, which results in tightening the strap 200a-b around the limb, i.e., pressure.

Significantly, any one of the described tensioning mechanisms 202a-b can be operatively connected to the strap, so as to enable rotatable manipulation, and thereby shortening and lengthening of the strap. Such manipulations by the tensioning mechanism 202a-b can include rotation of the free ends of the strap 200a-b to induce torque across the length of the strap 200a-b, which translates to pressure on the limb.

In some embodiments, the multiple tensioning mechanisms may include, without limitation, a lever, a windlass, a twist lock with incremental adjustments, a buckle, a ratchet, a button and button opening arrangement, and a friction fit mechanism. These different variations of tensioning mechanisms are described below. Furthermore, various coupling mechanisms 204, such as cables, screws, buckles, slots, buttons, magnets, clips, and friction fit mechanisms can be used to securely join the free ends of the strap with the variety of tensioning mechanisms.

Looking again at FIG. 5, the safety tourniquet 500 provides a tensioning mechanism that can be a simple lever 506 and cloth strap 502 that wraps around the limb. In operation, the wearer 108 simply twists the lever 506 in a first direction at the free ends of the strap 502. This works to reduce the length, and thereby create pressure around the limb. This integration of safety tourniquet 500 into a protective garment 102 creates a unique synergy, in which a dangerous operation that requires protective gear combines with medical-related equipment, i.e., tourniquet, sanitizer, sterile gauze pads.

In other embodiments, the simple lever 506 can include a windlass. In any case, the tensioning mechanism is simply an elongated member that concentrically attaches to the free ends of an attached strap 502. Rotation of the lever 506 shortens the portion of the strap 502 that wraps around the limb, which results in pressure on the limb. As the rotation increases, greater pressure is applied, which restricts blood flow towards the heart.

In alternative embodiments, a triangle or other anchoring member can attach to the protective garment to provide a docking space for the lever 506 to prevent the lever 506 from unwinding, and thereby loosening the strap around the limb.

Figure 6:
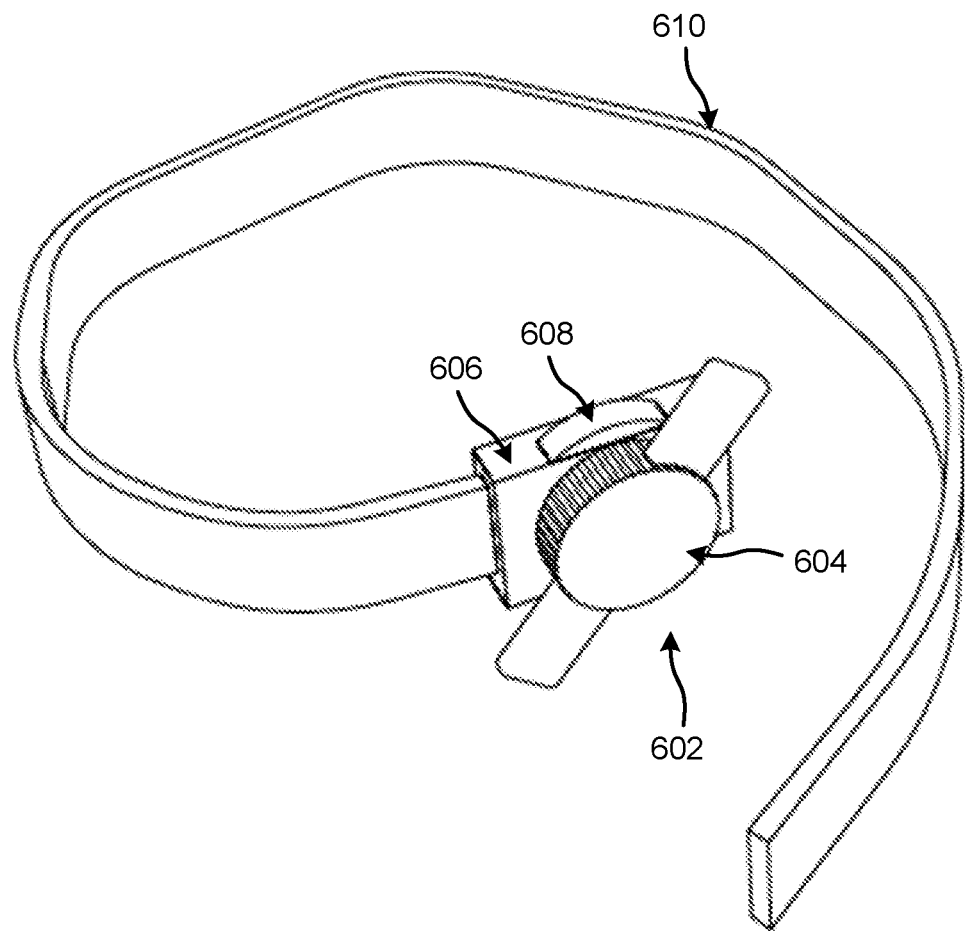
FIG. 6 illustrates a perspective view of an exemplary tensioning mechanism having a twist lock with incremental adjustments configuration, in accordance with an embodiment of the present disclosure.

As referenced in FIG. 6, a safety tourniquet 600 has a tensioning mechanism 602 configured as a twist lock with incremental adjustments. As illustrated, the tensioning mechanism 602 can easily be manipulated to generate inward compression on the limb by rotating a dial 604 connected to a gear device 606 that serves to tightening the strap 610 into high levels of circumferential tension when wrapped around the limb. A release switch 608 may be used to loosen the strap 610, once the need for restricting blood flow ceases. As with the aforementioned tensioning mechanism configurations, tensioning mechanism 602 is accessible from the outer face 112c on the limb sections 104a-b of protective garment 102.

Conversely, the direction of rotation can be reversed to lengthen the strap 610, which serves to loosen the pressure. This can be useful, for example, when professional medical personnel arrive with more sophisticated medical equipment, and the safety tourniquet 600 is no longer needed. However, any manipulation or mechanism that shortens or lengthens the length of the strap 610 around the leg may also be used.

Figure 7:
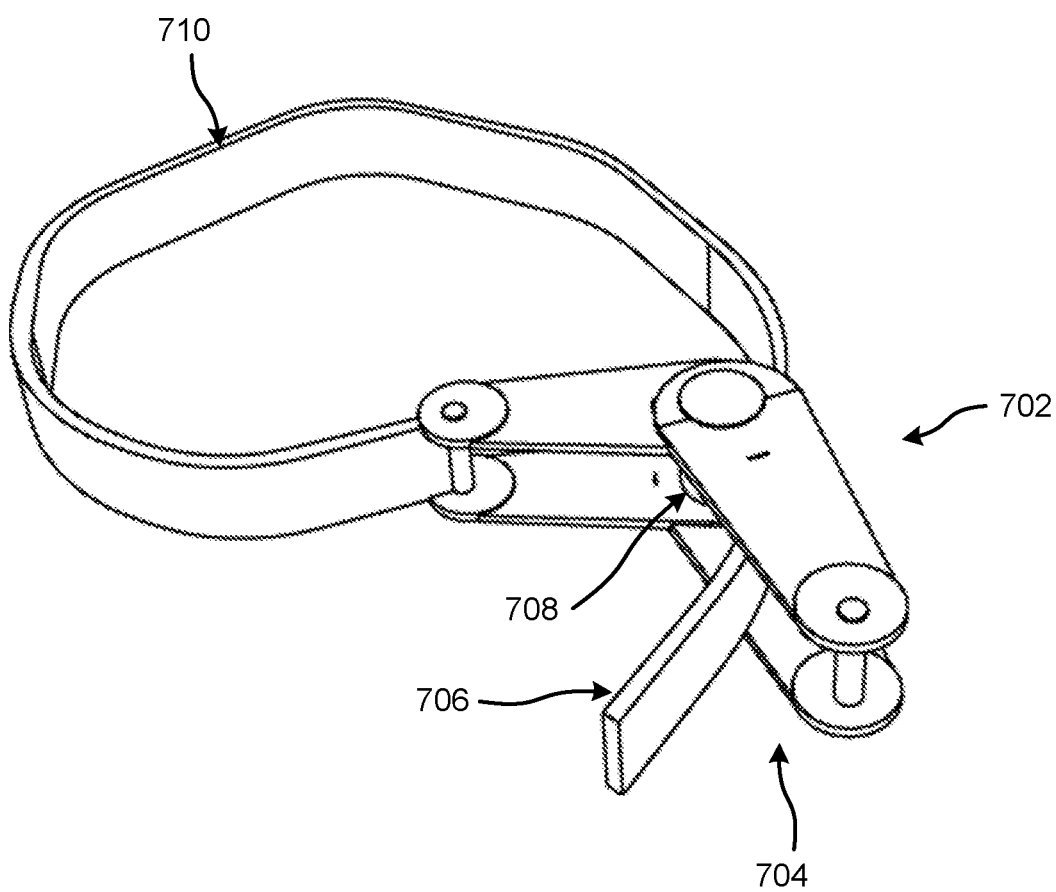
FIG. 7 illustrates a perspective view of an exemplary tensioning mechanism having a ratchet buckle configuration, in accordance with an embodiment of the present disclosure.

As FIG. 7 illustrates, a safety tourniquet 700 includes a tensioning mechanism 702, which can be a ratchet buckle. In this configuration, tensioning mechanism 702 utilizes a ratcheting-mechanism 704 having a lever 706 that urges the strap 710 through a plurality of teeth 708 until a desired tension is achieved with the strap around the limb. Such a ratcheting mechanism is configured to incrementally tighten and loosen the strap 710 wrapped around the limbs. In other embodiments, the ratcheting-mechanism 704 can include a wheel-shaped geared ratchet. In other embodiments, the ratcheting-mechanism 704 attaches to the free ends of the strap 710. The lever 706 is manipulated in a back-and-forth motion in which the teeth 708 and the free ends of the strap 710 lock together in increments in order to shorten the portion of the strap 710 that wraps around the limb. The ratcheting-mechanism 704 may also include a lock that restricts incremental motion in both directions.

Figure 8:
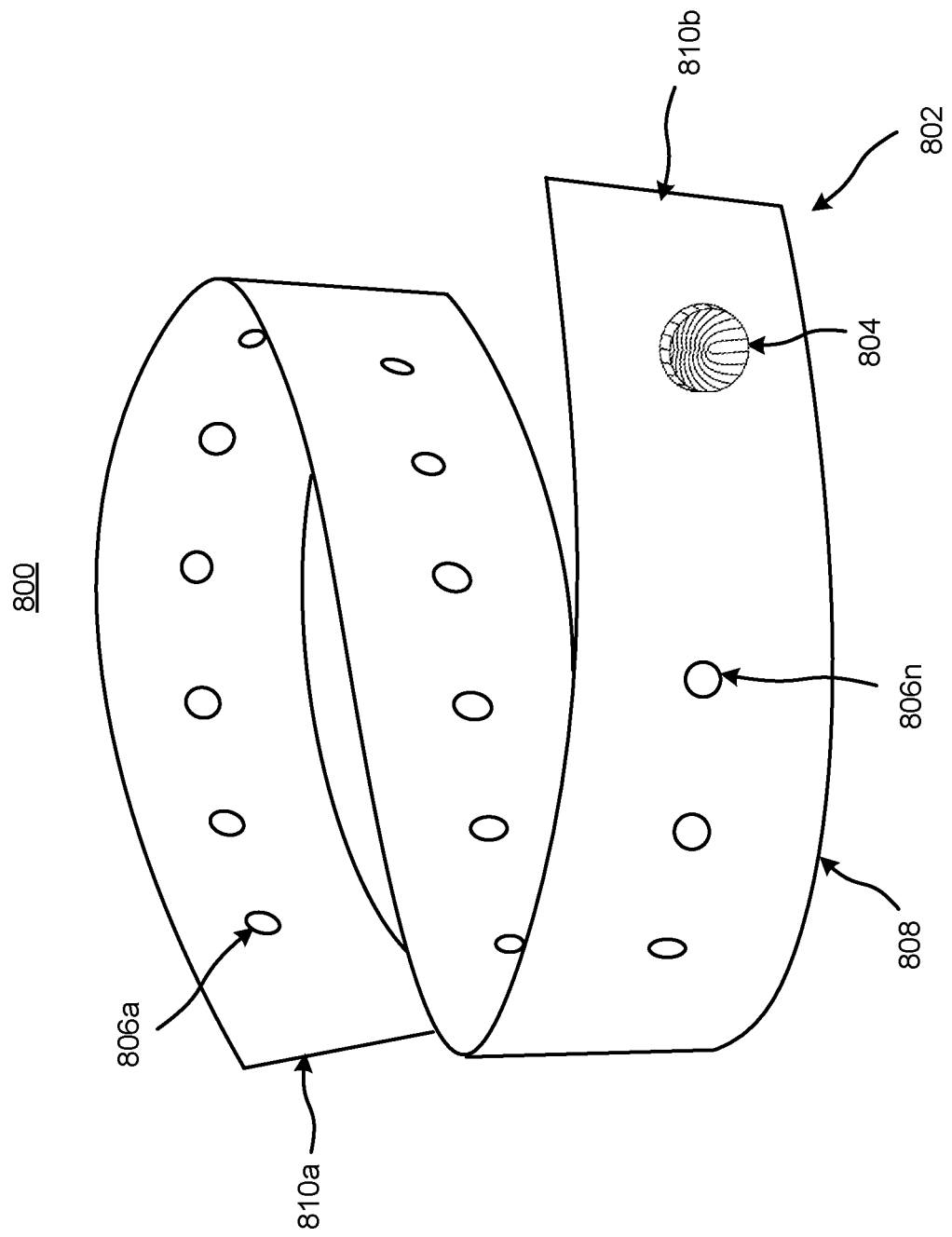
FIG. 8 illustrates a perspective view of an exemplary tensioning mechanism having a button and multi-hole configuration, in accordance with an embodiment of the present disclosure.

As FIG. 8 illustrates, a safety tourniquet 800 utilizes a tensioning mechanism 802 comprising a button 804 and multi-hole 806*a-n* arrangement. This configuration is integrated into a strap 808. One free end 810*a* of the strap 808 has a series of colinear holes 806*a*, 806*n*, while the opposing free end 810*b* has a button 804, or similar protrusion. In operation, the strap 808 is tightened to a desired pressure around the limb, where the button 804 is introduced into the corresponding hole 806*n* to firmly secure the strap 808 around the limb.

Figure 9:
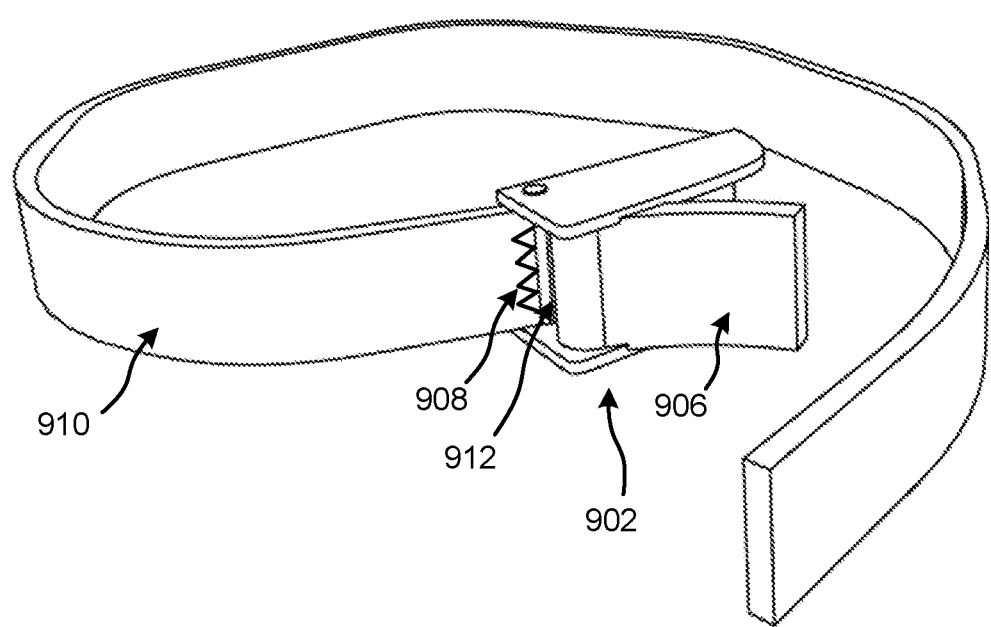
FIG. 9 illustrates a perspective view of an exemplary tensioning mechanism having a length-adjustable clinch buckle configuration, in accordance with an embodiment of the present disclosure.

Yet another type of tensioning mechanism is shown in FIG. 9. Here, the safety tourniquet 900 includes a tensioning mechanism 902 with a length-adjustable clinch buckle 904 configuration. The clinch buckle 904 is configured to tighten and loosen a strap 910 through slidable movement in and out of a pair of slots 912 in the buckle 904. The buckle 904 can include a locking mechanism 908, such as teeth, to restrain the strap 910 in a fixed position. A lever 906 can be ratcheted back and forth to advance the free end so of the strap 910 through the locking mechanism 908 to a desired tension around the limb. Thus, the wearer can slide the strap 910 through the slots 912 to achieve a desired pressure on the limb, and then fasten the strap 910 in the locking mechanism 908.

Figure 10:
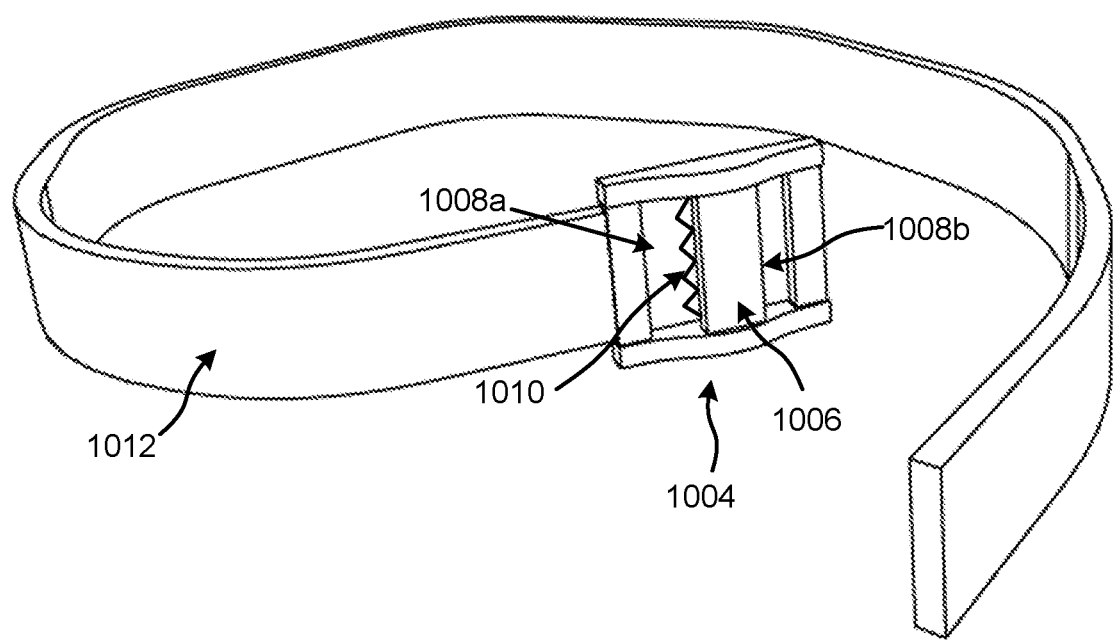
FIG. 10 illustrates a perspective view of an exemplary tensioning mechanism having a slip-lock buckle configuration, in accordance with an embodiment of the present disclosure.

Yet another type of tensioning mechanism is shown in FIG. 10. Here, the safety tourniquet 1000 includes a tensioning mechanism 1002 configured as a slip-lock buckle 1004. The slip-lock buckle 1004 includes a frame 1006 with a pair of slots 1008*a-b* that enables passage of the free ends of the strap 1012. Multiple teeth 1010 at the entry of slot 1008*a* retains the strap 1012 at a desired length, so as to achieve the necessary tension around the limb.

Figure 11:
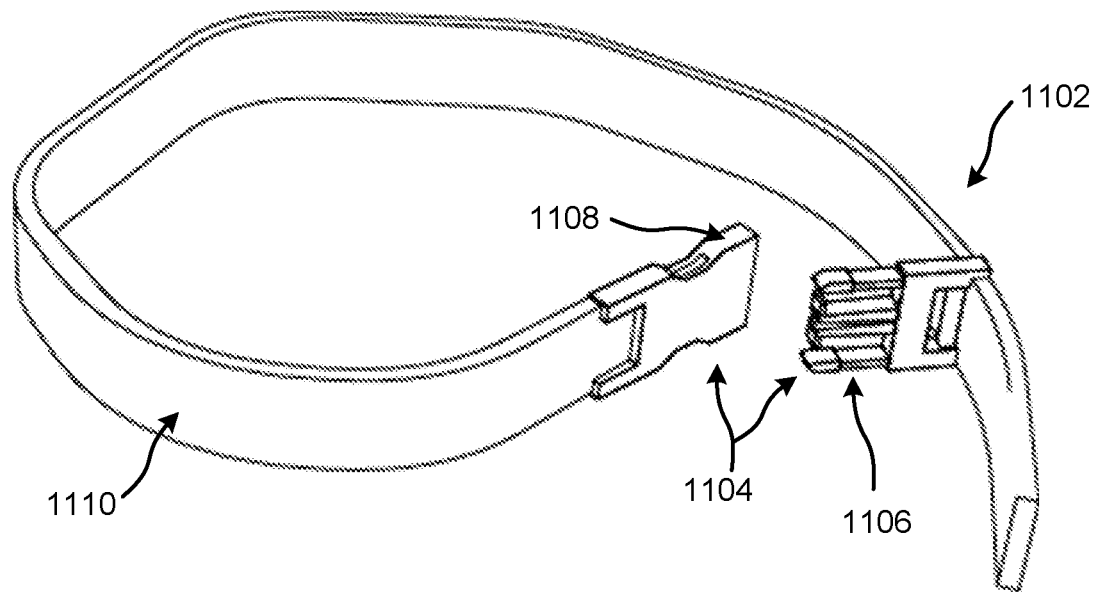
FIG. 11 illustrates a perspective view of an exemplary tensioning mechanism having an adjustable clip-buckle configuration, in accordance with an embodiment of the present disclosure.

FIG. 11 shows yet another type of tensioning mechanism. As illustrated, the safety tourniquet 1100 includes a tensioning mechanism 1102 configured as an adjustable clip-buckle 1104. The adjustable clip-buckle 1104 has a male end 1106 and a correlating female end 1108 that detachably couple to join the free ends of a strap 1110. The female end 1108 can have a length-adjusting buckle that enables the strap 1110 to be adjusted to a desired tension around the limb, before the male and female ends 1106, 1108 couple together.

Figure 12:
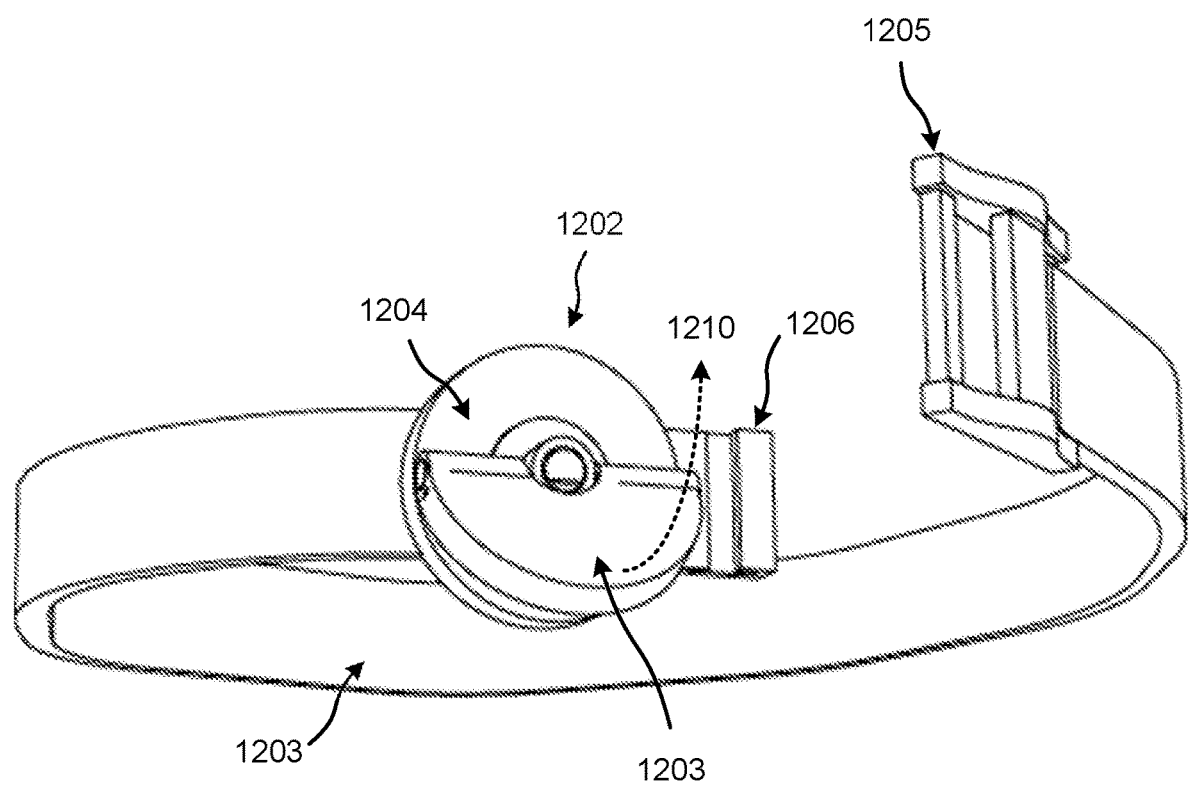
FIG. 12 illustrates a perspective view of an exemplary tensioning mechanism having a flip-up handle and twisting ratchet assembly, in accordance with an embodiment of the present disclosure.

FIG. 12 shows yet another type of tensioning mechanism. As illustrated, the safety tourniquet 1200 includes a tensioning mechanism 1202 having a flip-up handle 1203 and twisting ratchet assembly 1204. In addition, the safety tourniquet 1200 has a buckle member 1205 and a buckle connector member 1206 that detachably couple to join the free ends of a strap 1201. In operation, the flip-up handle 1203 is configured to 1) lay flat and rest against the ratchet 1204 when not in use and 2) flipped-up to a 90 degree position 1210, allowing the wearer to twist and rotate the twisting ratchet 1204 in either a clockwise or counter-clockwise direction to incrementally tighten or loosen the strap 1201, respectively, when the buckle member 1205 and the buckle connector member 1206 are connected.

Figure 13:
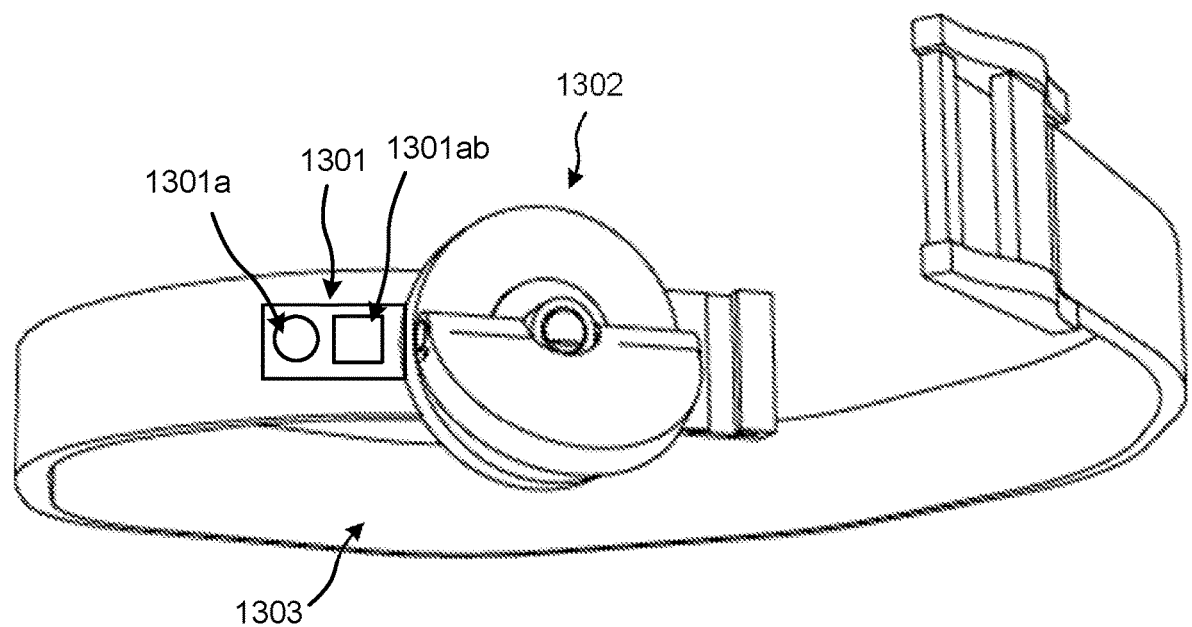
FIG. 13 illustrates a perspective view of an exemplary tensioning mechanism having an electronic alarm assembly coupled to the tensioning mechanism, in accordance with an embodiment of the present disclosure.

FIG. 13 illustrates a safety tourniquet 1300 having an electronic alarm assembly 1301 coupled to a tensioning mechanism 1302 for providing an adjustable tension to a strap 1303, according to an embodiment. In operation, once the strap 1303 is tightened by the tensioning mechanism 1302 via turning, twisting, pushing, or ratcheting the tensioning mechanism 1302, the electronic alarm assembly 1301 is automatically triggered and activated, generating an audible and/or visual SOS alarm to assist rescuers or coworkers in finding the wearer in case of severe injury. The electronic alarm assembly 1301 may include an audible alarm 1301*a* and/or a visual alarm 1301*b* which are triggered by the tensioning mechanism 1302. The electronic alarm assembly 1301 may also include a GPS tracking device and wireless communication hardware (not shown) for transmitting GPS coordinates to a mobile station or mobile device having programming and software applications which are configured to notify and transmit the GPS coordinates to rescuers or coworkers, providing them the exact location of the potentially injured wearer.

Figure 14:
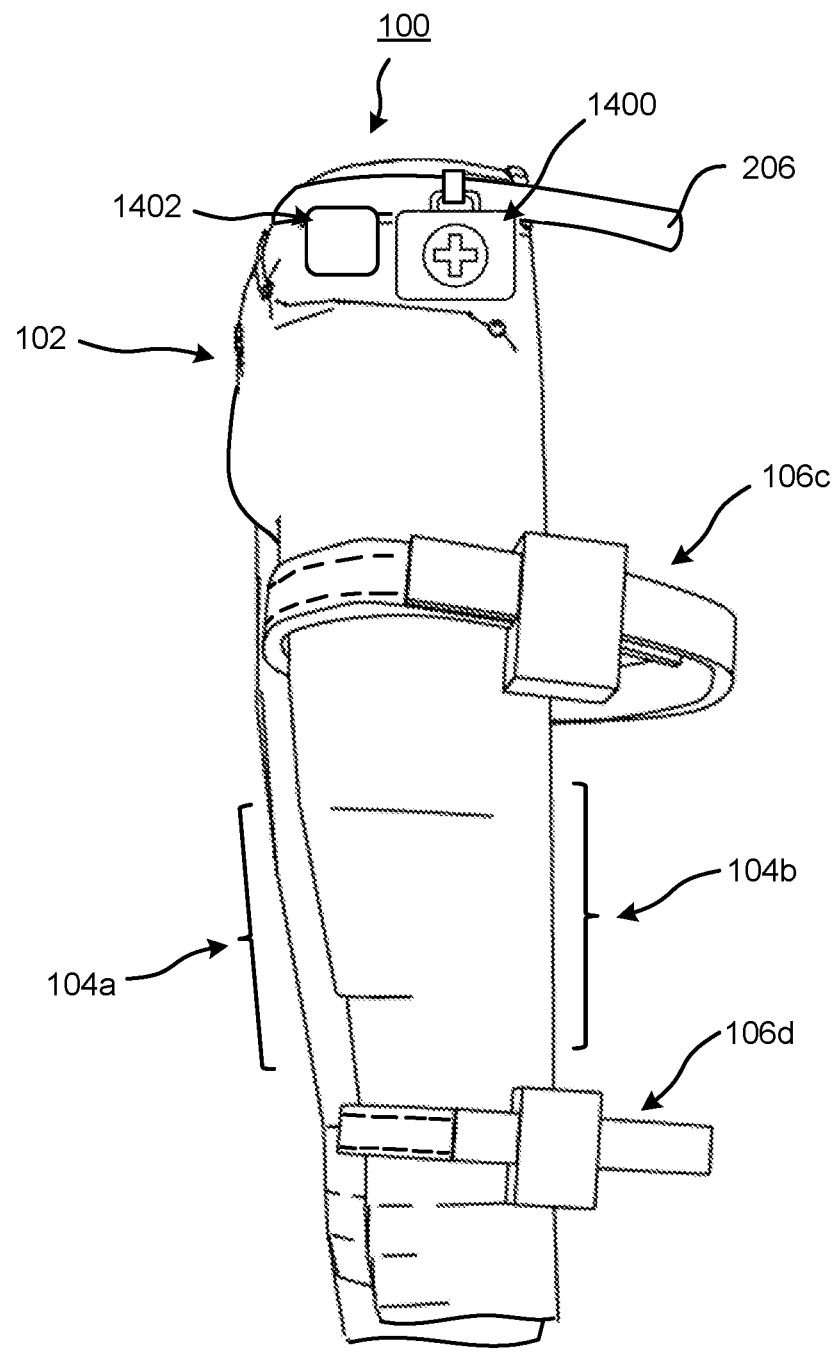
FIG. 14 illustrates a perspective view of the assembly having a medical kit and sanitizing gel pouch being attached to the chainsaw chaps, in accordance with an embodiment of the present disclosure.

In alternative embodiments, shown in FIG. 14, the assembly 100 also includes a medical kit 1400 that is removably insertable into a pocket in the protective garment 102. The position of the medical kit 1400 is such that it can be accessed easily by the wearer during an emergency in which the leg has been cut. In some embodiments, the medical kit 1400 may include inside, without limitation, a pair of scissors, a bandage, a sterile gauze pads, and a sanitizing agent.

In yet another embodiment, the assembly 100 provides a sanitizing gel pouch 1402 that attaches to the protective garment. The sanitizing gel pouch 1402 can be squeezed to dispense a sanitizing gel for application on the cut in the limb. However, in alternative embodiments, the sanitizing gel pouch 1402 and simply leave inserted into the medical kit 1400. In addition, the medical kit may include a stabilizing rod or splint kit for providing first aid should the user fracture or injure any of their limbs caused by either by the chainsaw or any accidental injury.

In other embodiments, each safety tourniquet 106*a*, 106*b*, 106*c*, 106*d* may be removable from the chainsaw chaps 102 and placed at different parts of the wearer's limbs including, for example, arms, ankle, or legs. Significantly, the tensioning mechanisms 202*a-b* are at the free ends of the strap 200*a-b*. This unique interchangeability allows for an eclectic variety of tensioning mechanisms to be used with the same strap 200*a-b* and protective garment. But interchangeability can be useful for multiple reasons. For example, a strap around the upper thigh would require greater torque, and thus a windlass would be effective. However, for the narrower calf region of the leg, a simple finger manipulated dial having incremental years could be used to tighten the strap around the calf region.

In yet another embodiment, each safety tourniquet 106*a*, 106*b*, 106*c*, 106*d* may have a self-tightening assembly that is self-activated when the wearer triggers the tension mechanism. For example, the self-tightening assembly may include a wounded spring assembly set to a predetermined tension and electro-mechanical devices having gear mechanisms that will tighten and engage the strap to a predetermined tension.

In another example of the advantages that interchangeability provides, a smaller tensioning mechanism may be preferred by a wearer is less cumbersome during chainsaw operations. However, another wearer would prefer a larger, easier to manipulate tensioning mechanism, focusing on the safety aspect thereof.

In operation, the wearer 108 intends to perform a chainsaw operation that requires protective gear. The wearer 108 dons a chainsaw chap, sliding the legs into the leg sections, and securing the waste section of the chaps to the waist. In alternative embodiments, a pair of suspenders may be used to retain the chainsaw chaps. The wearer then ensures that the integrated straps from the safety tourniquet wrap around the legs at the desired cross-sectional points. Generally, there will be a safety tourniquet at each thigh region of the leg, and a safety tourniquet further down the lower region of the leg.

During operation of the chainsaw, there could be an accident in which the blades kick back and strike the leg of the wearer. At this point, the blades of the chainsaw may have penetrated past the impact resistant layer, such that the leg is now bleeding. In a worst-case scenario, an artery in the leg has been cut. At this point, the wearer adjusts the strap between the cut and the heart.

A tensioning mechanism attached to the free ends of the strap is then manipulated, through lever rotation, back-and-forth ratcheting motion, or other means that would shorten the length of the strap around the leg. This tightening motion creates a pressure around the leg to stem the flow of blood until medical professionals arrive. Additionally, the wearer has access to a medical kit and/or a sanitizing gel pouch that are fitted inside a pocket of the chainsaw chaps, or attached thereto.

In conclusion, the assembly 100 provides a safety tourniquet that circumferentially integrates into a pair of chainsaw chaps for applying pressure to an injured limb. The safety tourniquet has a resilient strap that circumferentially integrates into the limb sections of the chaps. The strap is configured to wrap around the limb of the wearer directly, and without separation from the chaps. The safety tourniquet also has one or more tensioning mechanisms that are operatively attached to the strap.

In one possible embodiment, the assembly 100 provides an eclectic assortment of tensioning mechanisms to tighten and loosen the strap around the limb. In other embodiments, the tensioning mechanism can be interchanged to accommodate different pressure requirements, spacing around the chaps, and material and budgetary parameters. A medical kit and/or a sanitization pouch can detachably attach to the chaps, for easy retrieval thereof.

As used in the specification and the appended claims, the singular forms "a", "an", and "the" included plural referents unless the context clearly dictates otherwise.

The foregoing disclosure has been provided merely for the purpose of explanation and is in no way to be construed as limiting of the present disclosure. Although the present disclosure has been shown and described with respect to several preferred embodiments thereof, various changes, omissions, and additions to the form and detail thereof, may be made therein, without departing from the spirit and scope of the disclosure. It is understood that the words which have been used herein are words of description and illustration, rather than words of limitation. Changes may be made, within the purview of the appended claims, as presently stated and as amended, without departing from the scope and spirit of the present disclosure in its aspects.

Other embodiments and modifications of the present disclosure may occur to those of ordinary skill in the art in view of these teachings. Accordingly, the disclosure is to be limited only by the following claims which include all other such embodiments and modifications when viewed in conjunction with the above specifications and accompanying drawings.

What is claimed is:

1. A wearable safety tourniquet assembly, comprising:
a protective garment having:
multiple elongated limb sections configured to protect limbs of a wearer, the limb sections having a front face, an inner face, and an outer face;
multiple safety tourniquets, each safety tourniquet having:
a resilient strap being circumferentially and fixedly integrated into the limb sections of the protective garment, the strap operable to wrap around a portion of each limb of the wearer; and
a tensioning mechanism being operatively connected to the strap, the tensioning mechanism being oriented towards the outer face of the limb sections, wherein the tensioning mechanisms is configured to tighten the strap around each limb to stem the flow of blood, wherein an audible and/or visual alarm is coupled to the tensioning mechanism and triggered by the tensioning mechanism when the tensioning mechanism is incrementally tightened.

2. The assembly of claim 1, wherein the protective garment comprise a pair of chainsaw chaps.

3. The assembly of claim 1, wherein the limb sections of the protective garment comprise a cloth layer and an impact resistant layer.

4. The assembly of claim 3, wherein the strap integrates between the cloth layer and the impact resistant layer.

5. The assembly of claim 4, wherein the impact resistant layer comprises a fibrous material adapted to jam a saw chain of a chainsaw cutting through the cloth layer.

6. The assembly of claim 1, wherein the strap defines two free ends passing out of the protective garment through at least one opening.

7. The assembly of claim 1, wherein the strap has a front side and a back side.

8. The assembly of claim 1, wherein the outer face of each limb sections aligns with an outer region of each limb.

9. The assembly of claim 1, wherein each limb sections partially encircles each leg of the wearer.

10. The assembly of claim 1, wherein the tensioning mechanism includes a lever, a windlass, a dial, a buckle, a ratchet, a button and button opening arrangement, a flip-up handle and twisting ratchet assembly.

11. The assembly of claim 1, further comprising a medical kit removably insertable into a pocket in the protective garment.

12. The assembly of claim 11, wherein the medical kit includes at least one of the following: a pair of scissors, a bandage, sterile gauze pads, a splint kit, or a sanitizing agent.

13. A wearable safety tourniquet assembly, comprising:
a pair of chaps having:
multiple elongated leg sections configured to protect legs of a wearer, the leg sections having a front face, an inner face, and an outer face;
multiple safety tourniquets, each safety tourniquet having:
a resilient strap being circumferentially and fixedly integrated into the leg sections of the chaps, the strap operable to wrap around a portion of each leg of the wearer; and
a tensioning mechanism being operatively connected to the strap, the tensioning mechanism being oriented towards the outer face of the leg sections, wherein the tensioning mechanisms is configured to incrementally tighten the strap around each leg to stem the flow of blood, wherein an audible and/or visual alarm is coupled to the tensioning mechanism and triggered by the tensioning mechanism when the tensioning mechanism is incrementally tightened.

14. The assembly of claim 13, wherein the leg sections of the chaps comprise a cloth layer and an impact resistant layer.

15. The assembly of claim 14, wherein the strap integrates between the cloth layer and the impact resistant layer.

16. The assembly of claim 15, wherein the impact resistant layer comprises a fibrous material adapted to jam a saw chain of a chainsaw cutting through the cloth layer.

17. The assembly of claim 13, wherein the tensioning mechanism includes a lever, a windlass, a dial, a buckle, a ratchet, a button and button opening arrangement, a flip-up handle and twisting ratchet assembly.

18. The assembly of claim 13, further comprising a medical kit removably insertable into a pocket in the chaps.

* * * * *